(12) United States Patent
Maouche-Chretien et al.

(10) Patent No.: US 11,389,434 B2
(45) Date of Patent: Jul. 19, 2022

(54) METHODS AND PHARMACEUTICAL COMPOSITIONS FOR THE TREATMENT OF MAST CELL DISEASES

(71) Applicants: INSERM (INSTITUT NATIONAL DE LA SANTE ET DE LA RECHERCHE MEDICALE), Paris (FR); FONDATION IMAGINE, Paris (FR); UNIVERSITE PARIS DESCARTES, Paris (FR); ASSISTANCE PUBLIQUE-HOPITAUX DE PARIS (APHP), Paris (FR); CENTRE NATIONAL DE LA RECHERCHE SCIENTIFIQUE (CNRS), Paris (FR)

(72) Inventors: Leila Maouche-Chretien, Paris (FR); Christine Bodemer, Paris (FR); Olivier Hermine, Paris (FR); Laura Polivka, Paris (FR)

(73) Assignees: INSERM, Paris (FR); FONDATION IMAGINE, Paris (FR); UNIVERSITE PARIS DESCARTES, Paris (FR); ASSISTANCE PUBLIQUE-HOPITAUX DE PARIS (APHP), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 8 days.

(21) Appl. No.: 16/614,595

(22) PCT Filed: May 17, 2018

(86) PCT No.: PCT/EP2018/062889
§ 371 (c)(1),
(2) Date: Nov. 18, 2019

(87) PCT Pub. No.: WO2018/211007
PCT Pub. Date: Nov. 22, 2018

(65) Prior Publication Data
US 2020/0108053 A1    Apr. 9, 2020

(30) Foreign Application Priority Data
May 18, 2017 (EP) .................................. 17305573

(51) Int. Cl.
| A61K 31/4402 | (2006.01) |
| A61K 31/506 | (2006.01) |
| A61P 37/06 | (2006.01) |
| A61K 45/06 | (2006.01) |

(52) U.S. Cl.
CPC ........ *A61K 31/4402* (2013.01); *A61K 31/506* (2013.01); *A61P 37/06* (2018.01); *A61K 45/06* (2013.01)

(58) Field of Classification Search
CPC .... A61K 31/4402; A61K 31/506; A61P 37/06
See application file for complete search history.

(56) References Cited

U.S. PATENT DOCUMENTS

| 2010/0216828 A1* | 8/2010 | Dierks ................... A61K 31/66 514/275 |
| 2014/0315920 A1 | 10/2014 | Nocholas et al. |
| 2015/0225476 A1* | 8/2015 | Curotto de Lafaille ..................... A61K 39/3955 424/131.1 |

FOREIGN PATENT DOCUMENTS

| WO | 2003/011219 A2 | 2/2003 |
| WO | 2007/024971 A2 | 3/2007 |
| WO | 2007024971 | * 3/2007 |
| WO | 2008/154259 A1 | 12/2008 |
| WO | 2009/026075 A1 | 2/2009 |
| WO | 2009/130422 A2 | 10/2009 |
| WO | 2010/037715 A1 | 4/2010 |
| WO | 2012/059526 A1 | 5/2012 |
| WO | 2013/112859 A1 | 8/2013 |

OTHER PUBLICATIONS

Zhou et al: "Arsenic trioxide, a potent inhibitor of NR-[kappa]B, abrogates allergen-induced airway hyperresponsiveness and inflammation", Respiratory Research, vol. 7, No. 1, p. 146, Dec. 20, 2006.
Endo et al: "Psoriatic skin expresses the transcription factor Gli1: possible contribution of decreased neurofibromin expression", British Journal of Dermatology, vol. 154, No. 4, pp. 619-623, Apr. 2006.
Gotlib et al: "Efficacy and Safety of Midostaurin in Advanced Systemic Mastocytosis", New England Journal of Medicine, vol. 374, No. 26, pp. 2530-2541, Jun. 30, 2016.

* cited by examiner

*Primary Examiner* — Tracy Vivlemore
*Assistant Examiner* — Ebenezer O Sackey
(74) *Attorney, Agent, or Firm* — WC&F IP

(57) ABSTRACT

The inventors demonstrate for the first time the activation of the Hedgehog (HH) signaling pathway in normal and abnormal human mast cells (MCs). These results prompt the inventors to explore the consequence of the inhibition of the HH pathway, especially the canonical pathway, on MC proliferation. They demonstrate that Hedgehog inhibitors inhibit proliferation and induces apoptosis of mast cells. Accordingly the present invention relates to a method of treating a mast cell disease in a patient in need there of comprising administering to the patient a therapeutically effective amount of a Hedgehog inhibitor.

7 Claims, 11 Drawing Sheets

METHODS AND PHARMACEUTICAL COMPOSITIONS FOR THE TREATMENT OF MAST CELL DISEASES

FIELD OF THE INVENTION

Figure 1A:
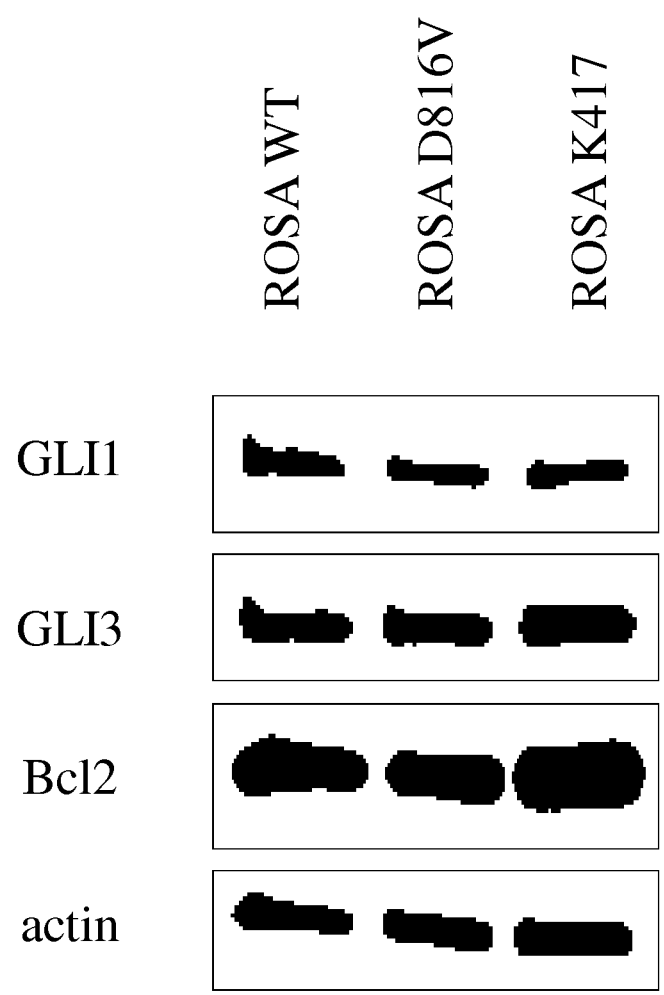

The present invention relates to methods and pharmaceutical compositions for the treatment of mast cell diseases.

BACKGROUND OF THE INVENTION

Mast cell diseases represent a particular concern in human health. For instance, mastocytosis is a disease characterized by the pathologic proliferation and accumulation of abnormal mast cells in one or more tissues. There are two forms of mastocytosis: cutaneous mastocytosis (CM) with limited involvement in the skin (more common in children) and systemic mastocytosis (SM). In SM, mastocytes accumulate in one or more extracutaneous tissues. SM represents 10% of mast cell disease and the majority (80%) of SM present the gain-of-function D816V mutation of the tyrosine kinase receptor KIT inducing constitutive activation of KIT signaling independently of SCF activation. This mutation results in increased production of mast cells and accumulation in extracutaneous organs that might results in organ failure (bone marrow, lymph nodes, liver, gastointestinal tract, spleen). Unfortunately, activating D816V KIT mutation is known to be associated with resistance to the currently available tyrosine kinase inhibitor (TKI) treatment for SM, approved by FDA: Imatinib. New efficient therapeutics are thus a priority for the treatment of mastocytosis.

The Hedgehog signaling pathway plays a key role in embryonic cells and is one of the key regulators of animal development. There are three Hedgehog proteins (Hh) associated with the Hedgehog signaling pathway, Sonic Hedgehog (Shh), Indian Hedgehog (Ihh) and Desert Hedgehog (Dhh). The Hedgehog proteins bind to the Patched-1 receptor. The Patched-1 receptor inhibits Smo activity and upon binding of a Hedgehog protein with Patched-1 this inhibition is alleviated, leading to activation of the GLI transcription factors Gli1, Gli2 and Gli3 which are involved in cell fate determination and proliferation. Aberrant activation of the hedgehog pathway has been implicated in patients suffering from a range of cancers, for example Basal cell carcinoma, pancreatic cancer, medulloblastoma, small cell lung cancer and prostate cancer. However, the role of this signaling pathway has not yet been investigated in mastocytosis.

SUMMARY OF THE INVENTION

The present invention relates to methods and pharmaceutical compositions for the treatment of mast cell diseases. In particular, the present invention is defined by the claims.

DETAILED DESCRIPTION OF THE INVENTION

The present invention relates a method of treating a mast cell disease in a patient in need there of comprising administering to the patient a therapeutically effective amount of a Hedgehog inhibitor.

As used herein, the term "mast cell" refers to a hematopoietic derived cell that mediates hypersensitivity reactions. Mast cells are characterized by the presence of cytoplasmic granules (histamine, chondroitin sulfate, proteases) that mediate hypersensitivity reactions, high levels of the receptor for IgE (FceRI), and require stem cell factor and IL3 (cytokines) for development. Mature mast cells are not found in the circulation, but reside in a variety of tissues throughout the body.

As used herein, the term "mast cell disease" refers to any disease characterized by pathological mast cell proliferation and/or activation (e.g. degranulation). Examples of mast cells diseases include any disease selected from the group consisting of mast cell activation syndrome; mastocytosis; idiopathic urticaria; chronic urticaria; atopic dermatitis; idiopathic anaphylaxis; Ig-E and non Ig-E mediated anaphylaxis; angioedema; allergic disorders; irritable bowel syndrome; mastocytic gastroenteritis; mastocytic colitis; fibromyalgia; kidney fibrosis; atherosclerosis; myocardial ischemia; hypertension; congestive heart failure; pruritus; chronic pruritus; pruritus secondary to chronic kidney failure; heart, vascular, intestinal, brain, kidney, liver, pancreas, muscle, bone and skin conditions associated with mast cells; CNS diseases such as Parkinson's disease and Alzheimer's disease; metabolic diseases such as diabetes; sickle cell disease; autism; chronic fatigue syndrome; lupus; chronic lyme disease; interstitial cystitis; multiple sclerosis; cancer; migraine headaches; psoriasis; eosinophilic esophagitis; eosinophilic gastroenteritis; Churg-Strauss syndrome; hypereosinophilic syndrome; eosinophilic fasciitis; eosinophilic gastrointestinal disorders; chronic idiopathic urticaria; myocarditis; Hirschsprung's-associated enterocolitis; postoperative ileus; wound healing; stroke; transient ischemic attack; pain; neuralgia; peripheral neuropathy; acute coronary syndromes; pancreatitis; dermatomyositis; fibrotic skin diseases; pain associated with cancer; ulcerative colitis; inflammatory bowel disease; radiation colitis; celiac disease; gluten enteropathy; radiation cystitis; painful bladder syndrome; hepatitis; hepatic fibrosis; cirrhosis; rheumatoid arthritis; lupus erythematosus; and vasculitis.

As used herein, the term "mastocytosis" has its general and describes a group of disorders in which pathologic mast cells accumulate in tissues. In particular, the term includes cutaneous mastocytosis and systemic mastocytosis (indolent or advanced). The pathogenesis of mastocytosis has been attributed to constitutive activation of the receptor tyrosine kinase KIT. In a large majority of mastocytosis patients, the deregulated tyrosine kinase activity of KIT is due to a mutation within the amino acid 816 of the protein (D816V) which also confers resistance to imatinib or imatinib mesylate in vitro and in vivo. In particular, the method of the present invention is particularly suitable for the treatment of systemic mastocytosis. As used herein, the term "systemic mastocytosis" or "SM" encompasses the 5 categories of SM defined by the World Health Organization (2016) according to their location and aggressiveness: indolent SM (ISM), smoldering SM (SSM), SM with an associated hematological neoplasm (SM-AHN), aggressive SM (ASM), and mast cell leukemia (MCL). The prognosis of patients with ASM and MCL is poor due to an aggressive nature of the cells and their tendency to detach from the main tumor. Many of these tumors, but not all, carry mutations in the tyrosine kinase receptor: KIT (stem cell factor receptor) that renders it constitutively activated leading to uncontrolled growth of the malignant mast cells (MCs). Clinical presentation in adult SM is heterogenous and includes skin disease (usually urticaria pigmentosa), mast cell mediator-release symptoms (headache, flushing, lightheadedness, syncope, anaphylaxis, etc), and direct or indirect organ damage (bone pain from lytic bone lesions, osteoporosis or bone fractures, hepatosplenomegaly, cytopenia from bone marrow involvement). In addition, around 20% of patients with SM may display significant and sometimes isolated blood eosinophilia. In particular, the method of the present invention is particularly suitable for the treatment of patients harbouring a KIT mutation (e.g. D816V or Delta 417-419 insY mutations). The term "KIT" has its general meaning in the art and refers to the human KIT. KIT is also known as "kit", "c-kit", "CD117" or "stem cell factor receptor". An exemplary native KIT amino acid sequence is provided in the UniProtKB/Swiss-Prot under accession number P10721). Methods of detecting KIT mutations are well known in the art and typically involves PCR assays.

As used herein, the term "mast cell activation syndrome" or "MCAS" has its general meaning in the art and encompasses a collection of clinical signs and symptoms resulting from the inappropriate activation of mast cells, wherein no proliferation or otherwise accumulation of mast cells is observed. According to an embodiment, MCAS corresponds to the syndrome defined by the Molderings criteria, or the Valent diagnostic criteria, or the Akin diagnostic criteria, as defined below. In a first embodiment, MCAS is defined according to Molderings et al. (Molderings et al., Journal of Hematology & Oncology, 2011, 4:10).

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a patient having a medical disorder or who ultimately may acquire the disorder, in order to prevent, cure, delay the onset of, reduce the severity of, or ameliorate one or more symptoms of a disorder or recurring disorder, or in order to prolong the survival of a patient beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the term "Hedgehog pathway" has its general meaning in the art and refers to Hedgehog (Hh) signal transduction. The main one is the canonical pathway which is initiated by the induction of the Hh precursor protein (45 kDa) in Hh-secreting cells, after which the precursor undergoes autocatalytic processing and modification. The precursor is cleaved to a 20 kDa N-terminal signal domain and a 25 kDa C-terminal catalytic domain. Subsequently, a cholesterol molecule is bound covalently to the carboxy terminus of the N-terminal domain, which is then secreted from the cytosol as a Hh ligand. On the surface of Hh-receiving cells there are two proteins of the pathway. One is Patched (Ptch), a twelve-pass transmembrane protein, interacts with the Hh ligand and the other is Smoothened (Smo), a seven pass transmembrane protein that is a signal transducer. In the absence of Hh ligands, Ptch interacts with Smo to inhibit its function and prevent activation of the downstream signaling cascade. Once the Hh ligand binds to Ptch along with Hh-interacting protein, Smo inhibition is released; this results in the activation of a downstream signaling cascade. This activation results in the release of a transcriptional factor GLI from a macromolecular complex on microtubules that includes the suppressor of fused, fused protein kinas A, GLI and possibly other components. GLI enters the nucleus and alters transcription of several genes, including those of the Hedgehog pathway. A non canonical pathway activates the Gli transcription factors in absence of HH ligands or any interaction between the HH receptors and HH ligands. For instance, the transforming growth factor beta (TGF-b) activates Gli1 and Gli2 factors through a functional Smad pathway and independently from Hh receptor signaling (Dennler S et al, Induction of sonic hedgehog mediators by transforming growth factor-beta: Smad3-dependent activation of Gli2 and Gli1 expression in vitro and in vivo. Cancer Res. 2007)

As used herein, the term "Hedgehog inhibitor" has its general meaning in the art and refers to one or more molecules known to inhibit the Hedgehog pathway. In particular, the Hedgehog inhibitor of the present invention is an inhibitor of the canonical pathway or an inhibitor of the non-canonical pathway.

Hedgehog inhibitors are well known in the art and are typically described in the following publications:

Xin M. Hedgehog inhibitors: a patent review (2013-present). Expert Opin Ther Pat. 2015 May; 25(5):549-65.

Hadden M K. Hedgehog pathway inhibitors: a patent review (2009-present). Expert Opin Ther Pat. 2013 March; 23(3): 345-61.

Tremblay M R, Nesler M, Weatherhead R, Castro A C. Recent patents for Hedgehog pathway inhibitors for the treatment of malignancy. Expert Opin Ther Pat. 2009 August; 19(8):1039-56.

Doan H Q, Silapunt S, Migden M R. Sonidegib, a novel smoothened inhibitor for the treatment of advanced basal cell carcinoma. Onco Targets Ther. 2016 Sep. 14; 9:5671-5678. Review. PubMed PMID: 27695345; PubMed Central PMCID: PMC5028081.

Silapunt S, Chen L, Migden M R. Hedgehog pathway inhibition in advanced basal cell carcinoma: latest evidence and clinical usefulness. Ther Adv Med Oncol. 2016 September; 8(5):375-82. doi: 10.1177/1758834016653605. Review. PubMed PMID: 27583029;

Proctor A E, Thompson L A, O'Bryant C L. Vismodegib: an inhibitor of the Hedgehog signaling pathway in the treatment of basal cell carcinoma. Ann Pharmacother. 2014 January; 48(1):99-106. doi: 10.1177/1060028013506696. Review. PubMed PMID: 24259609.

Xie J, Bartels C M, Barton S W, Gu D. Targeting hedgehog signaling in cancer: research and clinical developments. Onco Targets Ther. 2013 Oct. 10; 6:1425-35. doi: 10.2147/OTT.S34678. Review. PubMed PMID: 24143114; PubMed Central PMCID: PMC3797650.

Drenkhahn S K, Jackson G A, Slusarz A, Starkey N J, Lubahn D B. Inhibition of hedgehog/Gli signaling by botanicals: a review of compounds with potential hedgehog pathway inhibitory activities. Curr Cancer Drug Targets. 2013 June; 13(5):580-95. Review. PubMed PMID: 23675897.

Sahebjam S, Siu L L, Razak A A. The utility of hedgehog signaling pathway inhibition for cancer. Oncologist. 2012; 17(8):1090-9. doi: 10.1634/theoncologist.2011-0450. Review. PubMed PMID: 22851551; PubMed Central PMCID: PMC3425527.

Low J A, de Sauvage F J. Clinical experience with Hedgehog pathway inhibitors. J Clin Oncol. 2010 Dec. 20; 28(36):5321-6. doi: 10.1200/JCO.2010.27.9943. PubMed PMID: 21041712.

Heretsch P, Tzagkaroulaki L, Giannis A. Modulators of the hedgehog signalling pathway. Bioorg Med Chem. 2010 Sep. 15; 18(18):6613-24. doi: 10.1016/j.bmc.2010.07.038. Review. PubMed PMID: 20708941.

Doggrell S A. The hedgehog pathway inhibitor GDC-0449 shows potential in skin and other cancers. Expert Opin Investig Drugs. 2010 March; 19(3):451-4. doi:10.1517/13543780903571649. PubMed PMID: 20078247.

Yoneyama T, Arai M A, Sadhu S K, Ahmed F, Ishibashi M. Hedgehog inhibitors from Withania somnifera. Bioorg Med Chem Lett. 2015 Sep. 1; 25(17):3541-4. doi: 10.1016/j.bmcl.2015.06.081. PubMed PMID: 26169123.

Ohashi T, Tanaka Y, Shiokawa Z, Banno H, Tanaka T, Shibata S, Satoh Y, Yamakawa H, Yamamoto Y, Hattori H, Kondo S, Miyamoto M, Tojo H, Baba A, Sasaki S. Synthesis and evaluation of hedgehog signaling inhibitor with novel core system. Bioorg Med Chem. 2015 Aug. 1; 23(15):4777-91. doi: 10.1016/j.bmc.2015.05.036. PubMed PMID: 26094943.

Xin M, Zhang L, Tang F, Tu C, Wen J, Zhao X, Liu Z, Cheng L, Shen H. Design, synthesis, and evaluation of pyrrolo[2,1-f][1,2,4]triazine derivatives as novel hedgehog signaling pathway inhibitors. Bioorg Med Chem. 2014 Feb. 15; 22(4):1429-40. doi: 10.1016/j.bmc.2013.12.055. PubMed PMID: 24486203.

Ohashi T, Oguro Y, Tanaka T, Shiokawa Z, Tanaka Y, Shibata S, Sato Y, Yamakawa H, Hattori H, Yamamoto Y, Kondo S, Miyamoto M, Nishihara M, Ishimura Y, Tojo H, Baba A, Sasaki S. Discovery of the investigational drug TAK-441, a pyrrolo[3,2-c]pyridine derivative, as a highly potent and orally active hedgehog signaling inhibitor: modification of the core skeleton for improved solubility. Bioorg Med Chem. 2012 Sep. 15; 20(18):5507-17. doi: 10.1016/j.bmc.2012.07.034. PubMed PMID: 22898254.

Munchhof M J, Li Q, Shavnya A, Borzillo G V, Boyden T L, Jones C S, LaGreca S D, Martinez-Alsina L, Patel N, Pelletier K, Reiter L A, Robbins M D, Tkalcevic G T. Discovery of PF-04449913, a Potent and Orally Bioavailable Inhibitor of Smoothened. ACS Med Chem Lett. 2011 Dec. 21; 3(2):106-11. doi: 10.1021/ml2002423. PubMed PMID: 24900436; PubMed Central PMCID: PMC4025788.

Guerlet G, Spangenberg T, Mann A, Faure H, Ruat M. Synthesis and biological evaluation of desmethylveramiline, a micromolar Hedgehog inhibitor. Bioorg Med Chem Lett. 2011 Jun. 15; 21(12):3608-12. doi: 10.1016/j.bmcl.2011.04.103. PubMed PMID: 21592788.

Rifai Y, Arai M A, Sadhu S K, Ahmed F, Ishibashi M. New Hedgehog/GLI signalling inhibitors from *Excoecaria agallocha*. Bioorg Med Chem Lett. 2011 Jan. 15; 21(2):718-22. doi: 10.1016/j.bmcl.2010.11.126. PubMed PMID: 21190854.

Heretsch P, Tzagkaroulaki L, Giannis A. Modulators of the hedgehog signalling pathway. Bioorg Med Chem. 2010 Sep. 15; 18(18):6613-24. doi:10.1016/j.bmc.2010.07.038. Review. PubMed PMID: 20708941.

Pan S, Wu X, Jiang J, Gao W, Wan Y, Cheng D, Han D, Liu J, Englund N P, Wang Y, Peukert S, Miller-Moslin K, Yuan J, Guo R, Matsumoto M, Vattay A, Jiang Y, Tsao J, Sun F, Pferdekamper A C, Dodd S, Tuntland T, Maniara W, Kelleher J F 3rd, Yao Y M, Warmuth M, Williams J, Dorsch M. Discovery of NVP-LDE225, a Potent and Selective Smoothened Antagonist. ACS Med Chem Lett. 2010 Mar. 16; 1(3):130-4. doi: 10.1021/ml1000307. PubMed PMID: 24900187; PubMed Central PMCID: PMC4007689.

Peng L F, Stanton B Z, Maloof N, Wang X, Schreiber S L. Syntheses of aminoalcohol-derived macrocycles leading to a small-molecule binder to and inhibitor of Sonic Hedgehog. Bioorg Med Chem Lett. 2009 Nov. 15; 19(22):6319-25. doi: 10.1016/j.bmcl.2009.09.089. PubMed PMID: 19819139; PubMed Central PMCID: PMC2796117.

Robarge K D, Brunton S A, Castanedo G M, Cui Y, Dina M S, Goldsmith R, Gould S E, Guichert O, Gunzner J L, Halladay J, Jia W, Khojasteh C, Koehler M F, Kotkow K, La H, Lalonde R L, Lau K, Lee L, Marshall D, Marsters J C Jr, Murray L J, Qian C, Rubin L L, Salphati L, Stanley M S, Stibbard J H, Sutherlin D P, Ubhayaker S, Wang S, Wong S, Xie M. GDC-0449-a potent inhibitor of the hedgehog pathway. Bioorg Med Chem Lett. 2009 Oct. 1; 19(19):5576-81. doi: 10.1016/j.bmcl.2009.08.049. Erratum in: Bioorg Med Chem Lett. 2010 Jan. 15; 20(2):771. PubMed PMID: 19716296.

In some embodiments, the Hedgehog inhibitor is selected from the compounds described in the international patent applications WO2014191736 and WO2010147917.

Specific examples of Hedgehog inhibitors include but are not limited to zerumbone epoxide, staurosporinone, 6-hydroxystaurosporinone, arcyriaflavin C, 5,6-dihyroxyarcyriaflavin A, physalin F, physalin B, cyclopamine, HPI-1, HPI-2, HPI-3, and HPI-4, arsenic trioxide (ATO), sodium arsenite, phenylarsine, GANT-58, GANT-61, and zerumbone (Kim et al., 2010, PNAS, 107:13432-37; Beauchamp et al. 2011, JCI 121:148-60; Lauth et al 2007, PNAS 104:8455-60; Hosoya et al., 2008, ChemBioChem 9:1082-92; Hyman et al, 2009, 106:14132-37; and Mas et al, 2010, Biochem. Pharm. 80:712-23, all hereby incorporated by reference in their entirety). Other examples include vismodegib (GDC-0449, Genentech), BMS-833923 (XL139), IPI-926—Infinity Pharmaceuticals, Inc., LDE225, LEQ506—Novartis Pharmaceuticals, TAK-441 Millennium Pharmaceuticals, Inc., and PF-04449913—Pfizer, alone or in combination therapy.

Other examples of Hedgehog inhibitors include 4-fluoro-N-methyl-N-(I-(4-(I-methyl-1H-pyrazol-5-yl)phthalazin-1-yl)piperidin-4-yl)-2-(trifluoromethyl)benzamide, 4-fluoro-N-methyl-N-(I-(4-(I-methyl-1H-pyrazol-5-yl)phthalazin-1-yl)piperidin-4-yl)-2-(trifluoromethyl)benzamide hydrochloride.

In some embodiments, the Hedgehog inhibitor of the present invention is vismodegib characterized by the formula of:

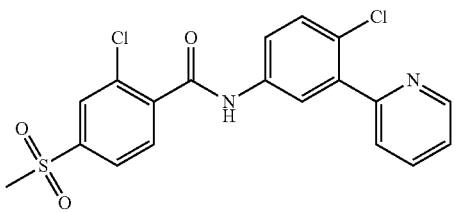 [SMILES: CS(=O)(=O)c1ccc(C(=O)Nc2ccc(Cl)c(-c3ccccn3)c2)c(Cl)c1]

By a "therapeutically effective amount" of the Hedgehog inhibitor of the invention as above described is meant a sufficient amount of the compound. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the Hedgehog inhibitor of the present invention is administered to the patient in combination with a tyrosine kinase inhibitor. As used herein, the term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art. Examples of tyrosine kinase inhibitors include but are not limited to PKC412 (midostaurin), afatinib, alitretinoin, axitinib, bafetinib, bexarotene, BI-2536, bosutinib, brivanib, canertinib, cediranib, CP724714, crizotinib, dasatinib, danusertib, dovitinib, E7080, erlotinib, everolimus, fostamatinib, gefitinib, imatinib, lapatinib, lestaurtinib, linsitinib, masitinib, motesanib, neratinib, nilotinib, NVP TAE-684, OSI-027, OSI-420, OSI-930, pazopanib, pelitinib, PF573228, regorafenib, romidepsin, ruxolitinib, saracatinib, sorafenib, sunitinib, TAE226, TAE684, tandutinib, telatinib, tautinib, temsirolimus, toceranib, tofacitinib, tozasertib, tretinoin, vandetanib, vatalanib, vemurafenib, vorinostat and WZ 4002. Additional tyrosine kinase inhibitors and related compounds suitable for use in the present invention are described in, for example, U.S. Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In particular, the Hedgehog inhibitor of the present invention is administered to the patient in combination with masitinib. The chemical name for masitinib is 4-(4-methylpiperazin-1-ylmethyl)-N-[4-methyl-3-(4-pyridin-3ylthiazol-2-ylamino)phenyl]benzamide—CAS number 790299-79-5. In some embodiments, the Hedgehog inhibitor of the present invention is administered to the patient in combination with PKC412 (midostaurin). As used herein, the term "PKC 412" or "midostaurin" has its general meaning in the art and refers to N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methylbenzamide (CAS number: 120685-11-2). The term is also known as CGP 41231, CGP 41251 and N-Benzoylstaurosporine. PKC 412 is a cell-permeable, reversible inhibitor of several serine/threonine and tyrosine kinases, including conventional PKC isoforms ($\alpha$, $\beta$, and $\gamma$), Syk, FLK1, Akt, PKA, c-Kit, C-Fgr, c-Src, FLT3, PDFR$\beta$, VEGFR1, and VEGFR2 with IC50 values ranging from 80-500 nM.

The Hedgehog inhibitor of the invention may be combined with pharmaceutically acceptable excipients, and optionally sustained-release matrices, such as biodegradable polymers, to form therapeutic compositions. "Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Galenic adaptations may be done for specific delivery in the small intestine or colon. Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising Hedgehog inhibitors of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The Hedgehog inhibitor of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifusoluble agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject. The Hedgehog inhibitor of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the Hedgehog inhibitors of the invention formulated for parenteral administration, such as intravenous or intramuscular injection, other pharmaceutically acceptable forms include, e.g. tablets or other solids for oral administration; liposomal formulations; time release capsules; and any other form currently used.

The invention will be further illustrated by the following figures and examples. However, these examples and figures should not be interpreted in any way as limiting the scope of the present invention.

FIGURES

Figure 1B:
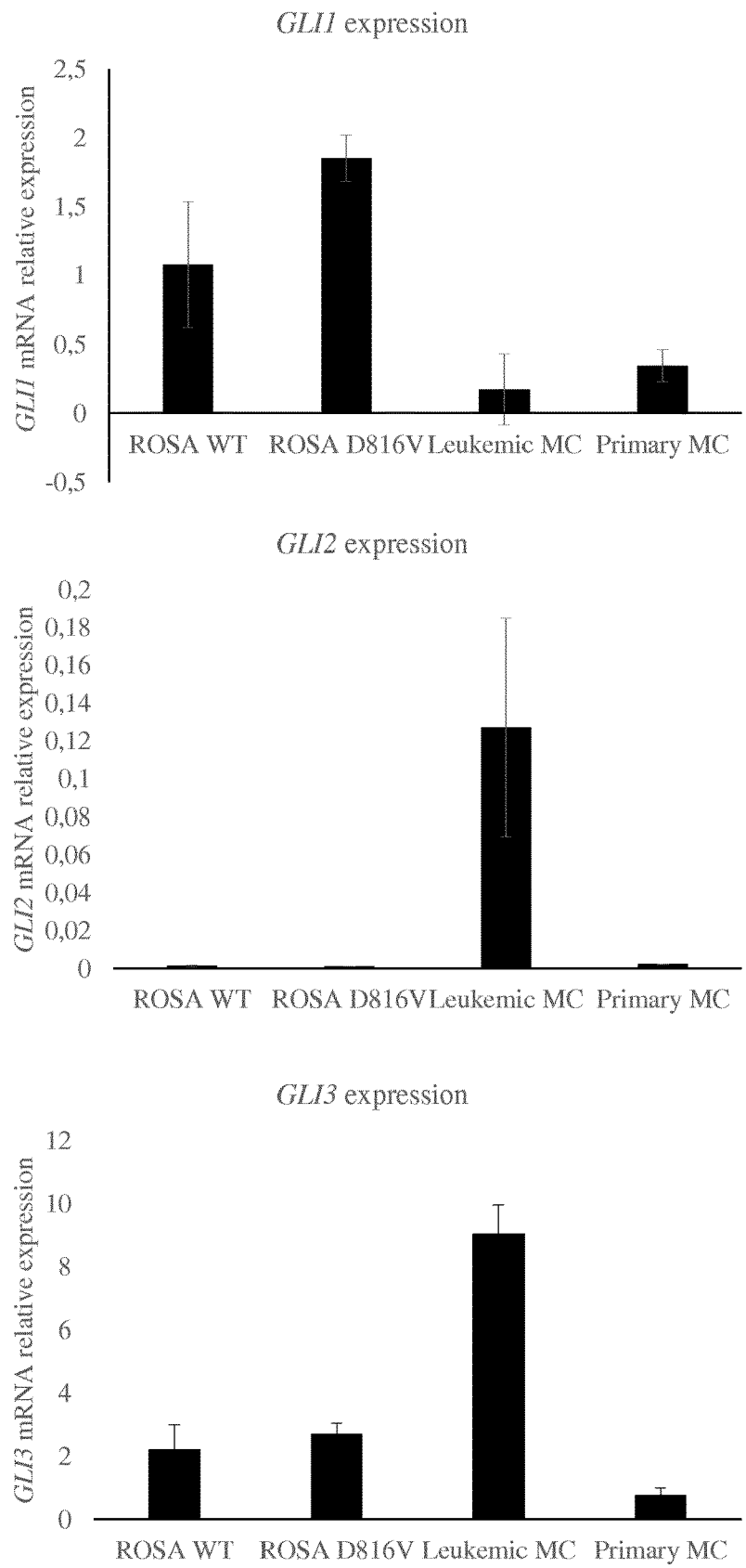

FIG. 1. Expression of hedgehog target genes a) Immunoblotting of GLI1, GLI3 and Bcl2 in ROSA KIT WT, ROSA KIT D816V and ROSA KIT K417 cell lines; b) Relative mRNA levels of GM, GLI2 and GLI3, normalized to actin mRNA, were performed by quantitative RT-PCR in ROSA KIT WT, ROSA KIT D816V cell lines, leukemic MC and primary MC. Three independent experiments were performed in triplicate. Data are represented as the mean±standard deviation.

Figure 2:
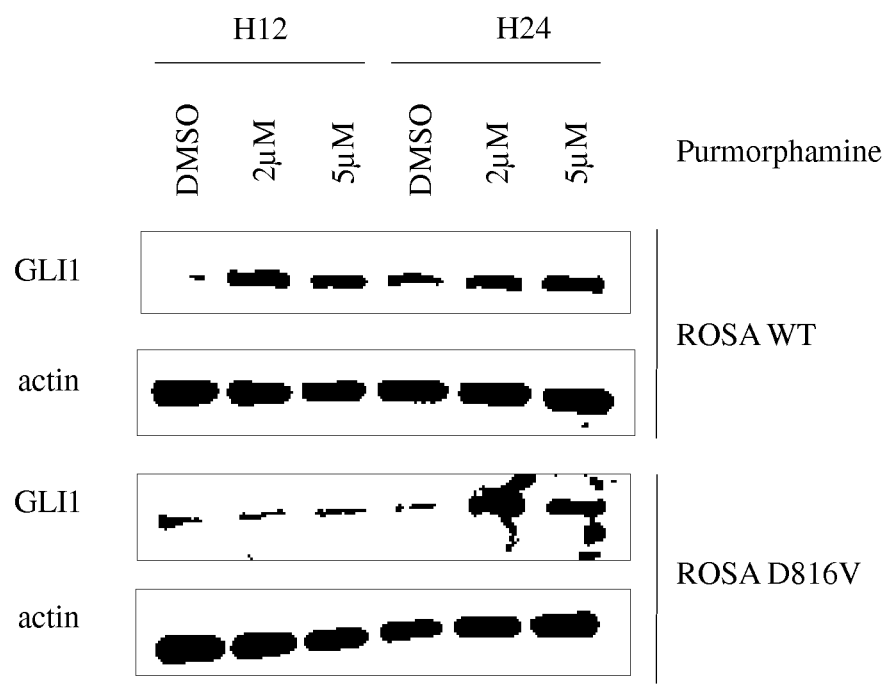
Figure 3A:
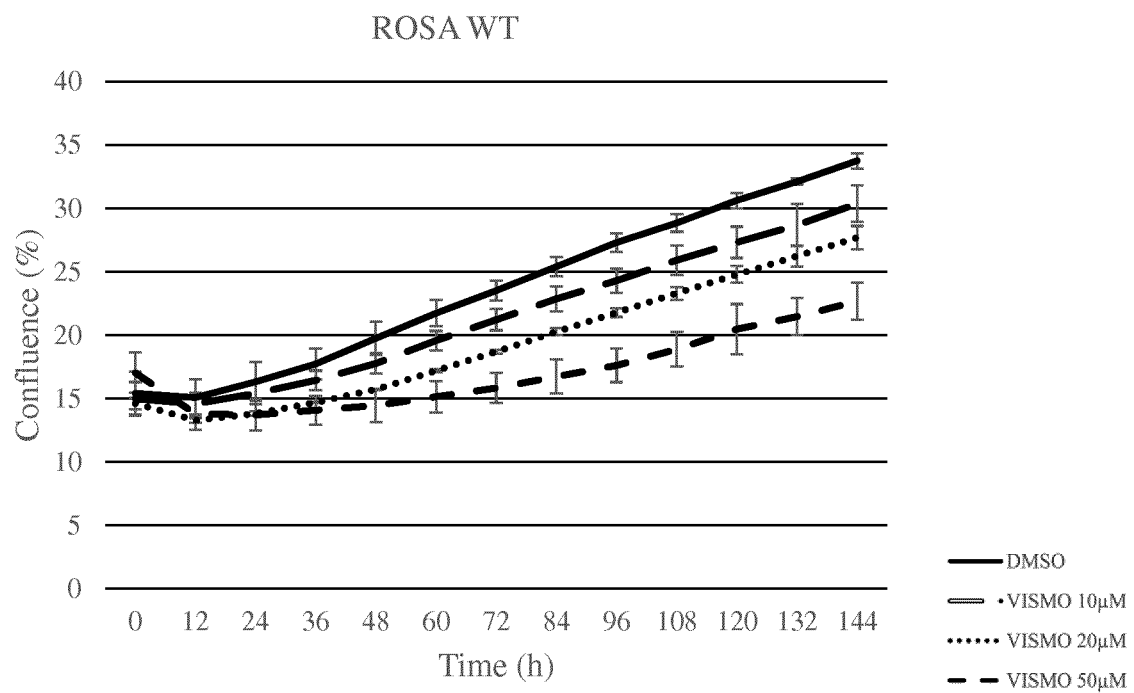
Figure 3B:
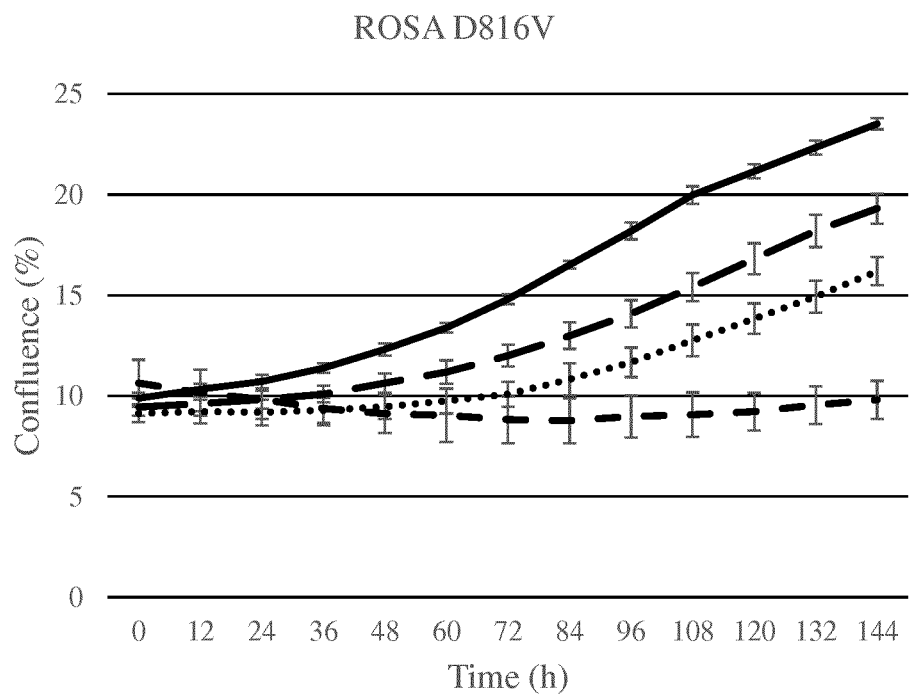
Figure 3C:
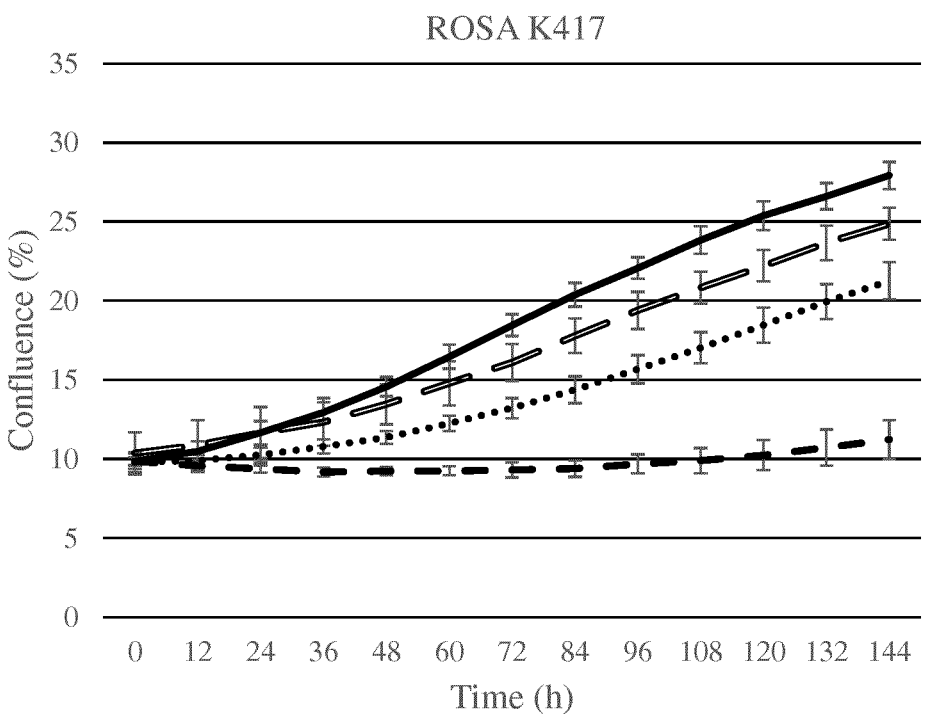
Figure 3D:
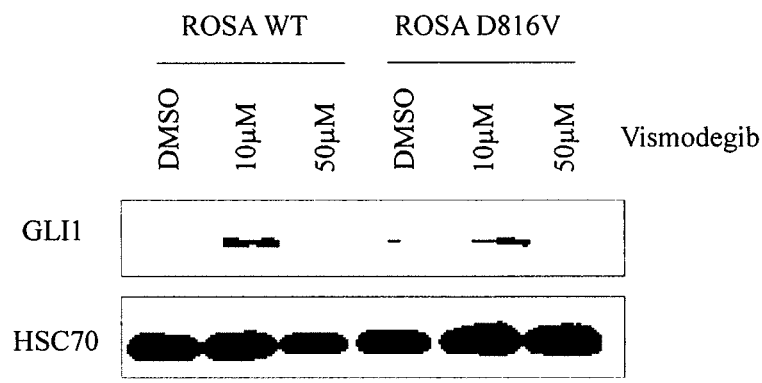
Figure 4A:
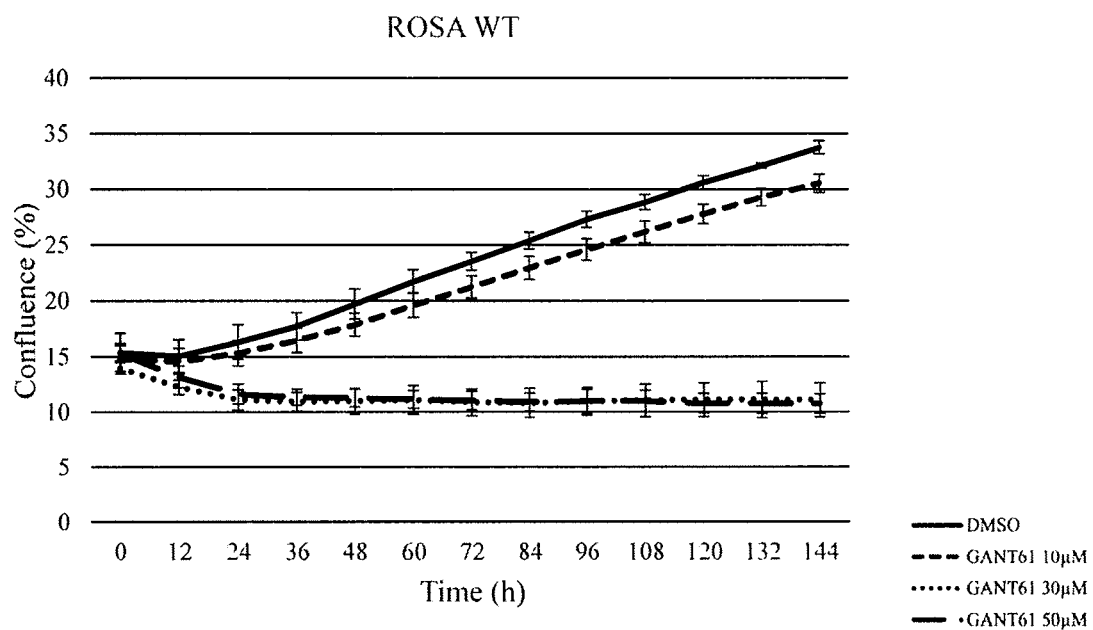
Figure 4B:
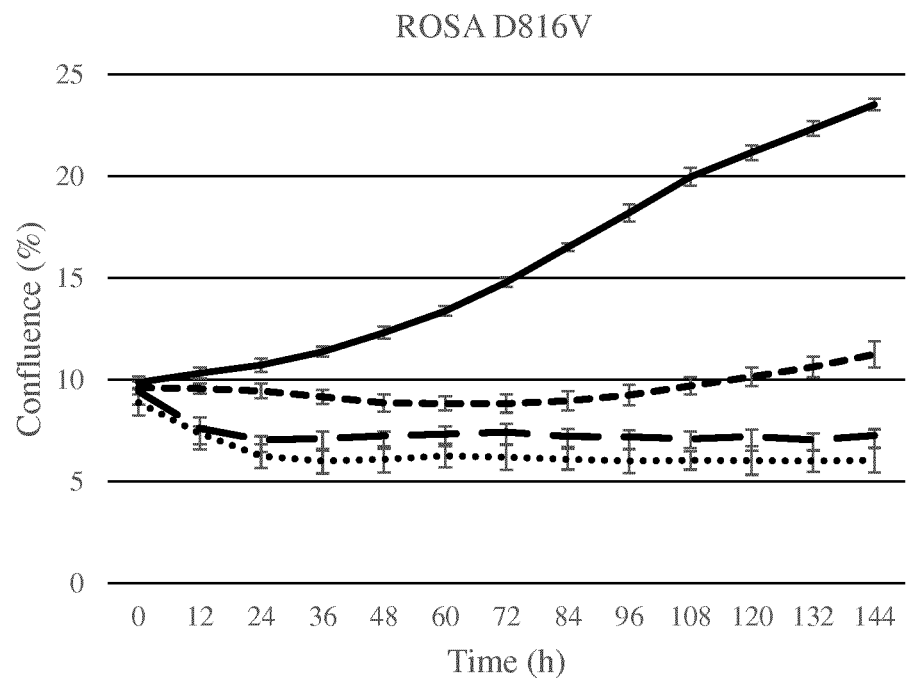
Figure 4C:
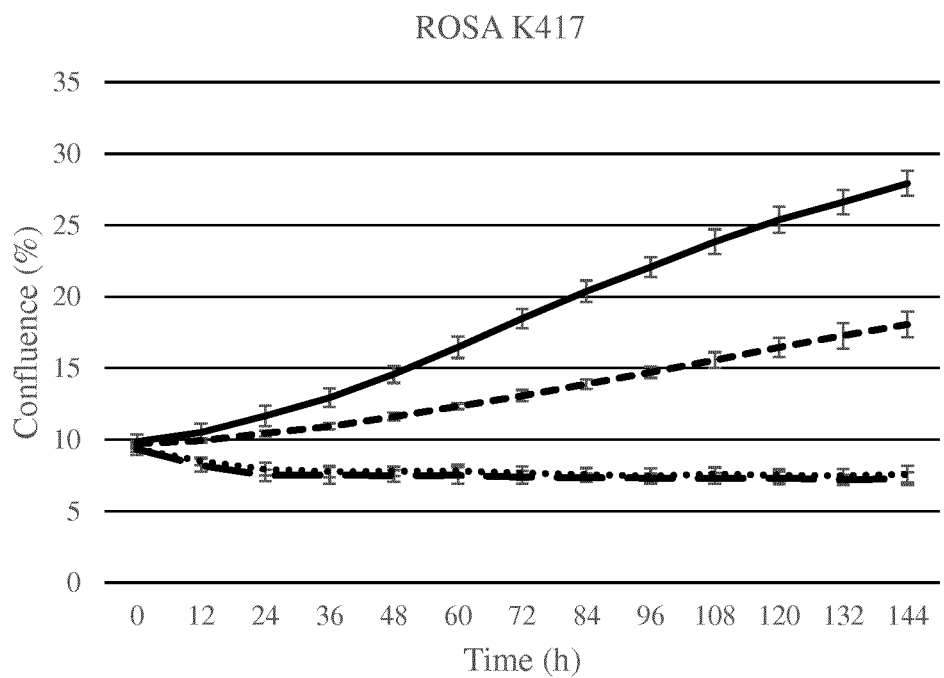
Figure 4D:
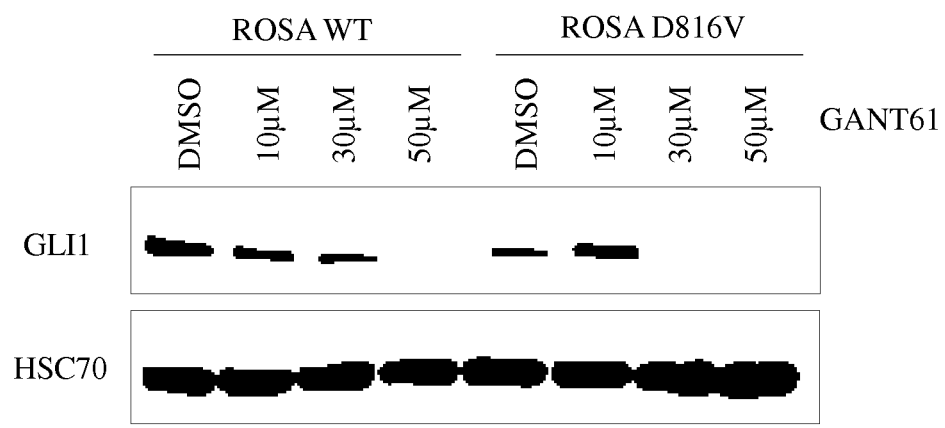

FIG. 2. Analysis of hedgehog signaling pathway following stimulation by purmorphamine Immunoblotting of GLI1 in ROSA KIT WT and KIT D816V cell lines following stimulation by purmorphamine (12 or 24 hours) at 2 or 5 µM.

FIG. 3. Vismodegib inhibits mast cells proliferation. a) Percentage of confluence of ROSA KIT WT treated with DMSO (control), vismodegib 10, 20 or 50 µM during 144 hours. b) Percentage of confluence of ROSA KIT D816V treated with DMSO (control), vismodegib 10, 20 or 50 µM during 144 hours. c) Percentage of confluence of ROSA KIT K417 treated with DMSO (control), vismodegib 10, 20 or 50 µM during 144 hours. d) Immunoblotting of GLI1 in ROSA KIT WT and D816V cell lines, treated with DMSO or vismodegib. Three independent experiments were performed in triplicate, using the IncuCyte® Live Cell Analysis system. Data are represented as the mean±standard deviation.

FIG. 4. GANT61 inhibits MC proliferation. A) Percentage of confluence of ROSA KIT WT treated with DMSO (control), GANT61 10, 30 or 50 µM during 144 hours. B) Percentage of confluence of ROSA KIT D816V treated with DMSO (control), GANT61 10, 30 or 50 µM during 144 hours. C) Percentage of confluence of ROSA KIT K417 treated with DMSO (control), GANT61 10, 30 or 50 µM during 144 hours. D) Immunoblotting of Gill in ROSA KIT WT and D816V cell lines, treated with DMSO or GANT61. Three independent experiments were performed in triplicate, using the IncuCyte® Live Cell Analysis system. Data are represented as the mean±standard deviation.

Figure 5A:
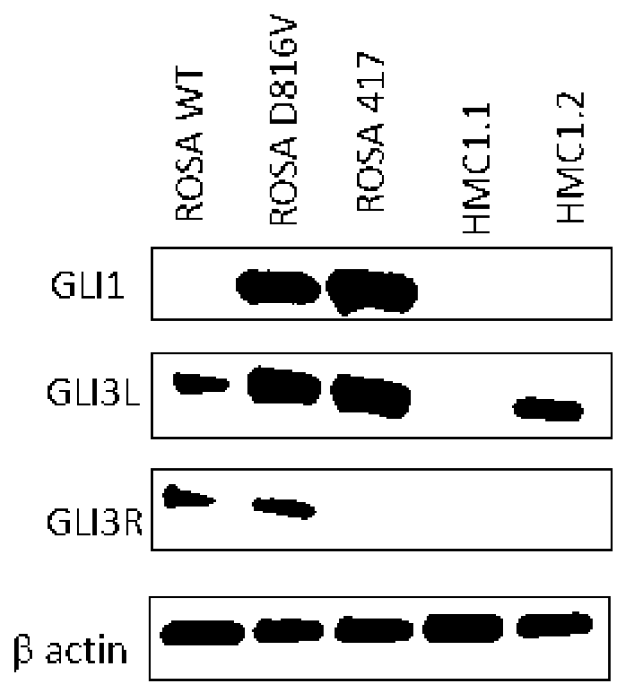
Figures 5B, 5C:
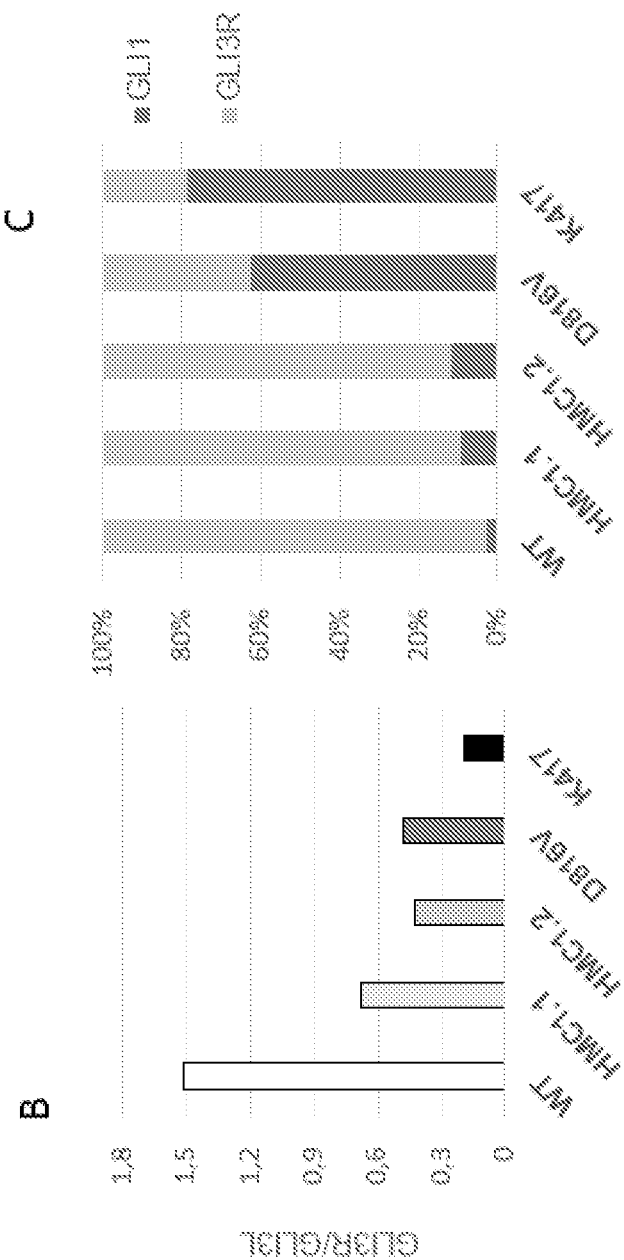

FIG. 5. Expression analysis of GLI transcription factors in different mast cell lineages carrying or not KIT-D816V mutation. A) Expression of GLI1, GLI2, GLI3L and GLI3R were determined by western blot analysis. Beta-Actin was used as a loading internal control in these experiments. GLI2 was not detected in any of the cell lineages (data not shown). B) The bar graph shows the ratio of GLI3R/GLI3L calculated from western blot data after normalization with beta—Actin. C) Expression level of GLI1 protein is inversely correlated to the expression level of GLI3R (the repressor form of GLI3) in mast cell lines.

Figure 6:
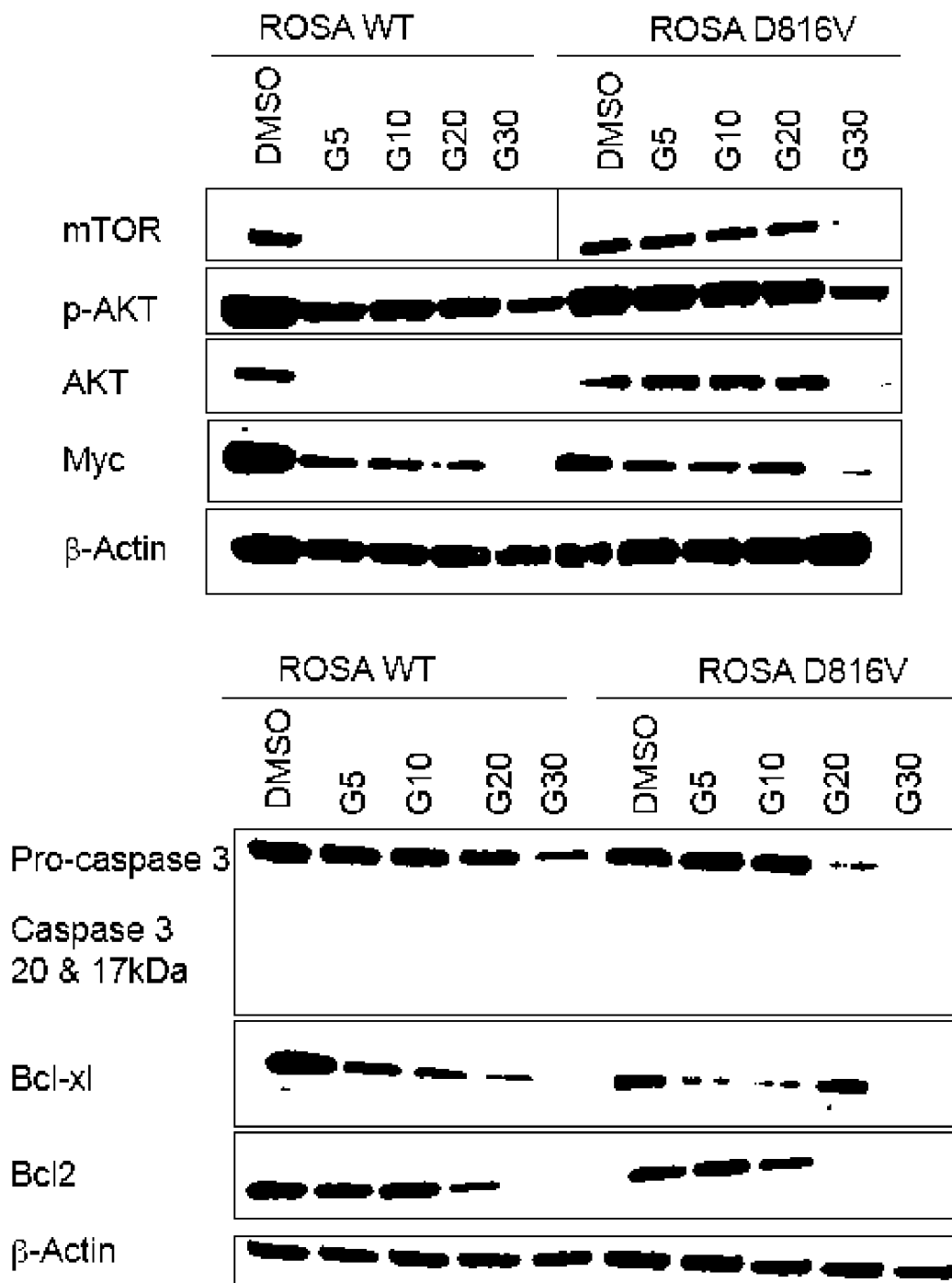

FIG. 6. GANT61 inhibits mast cells proliferation and induces mast cells apoptosis.

ROSA WT and ROSA D816V were treated with increasing doses of GANT 61 hedgehog inhibitor and the expression of proteins associated with cell proliferation or cell apoptosis was determined by western blot. Expression levels of mTOR, p-AKT, AKT, MYC(Top), Caspase3, BCL2, and BCLX-L (Bottom) proteins decreased, both in ROSA WT and ROSA D816V treated with GANT61 in a dose dependent manner. bActin was used as a loading control.

Figure 7:
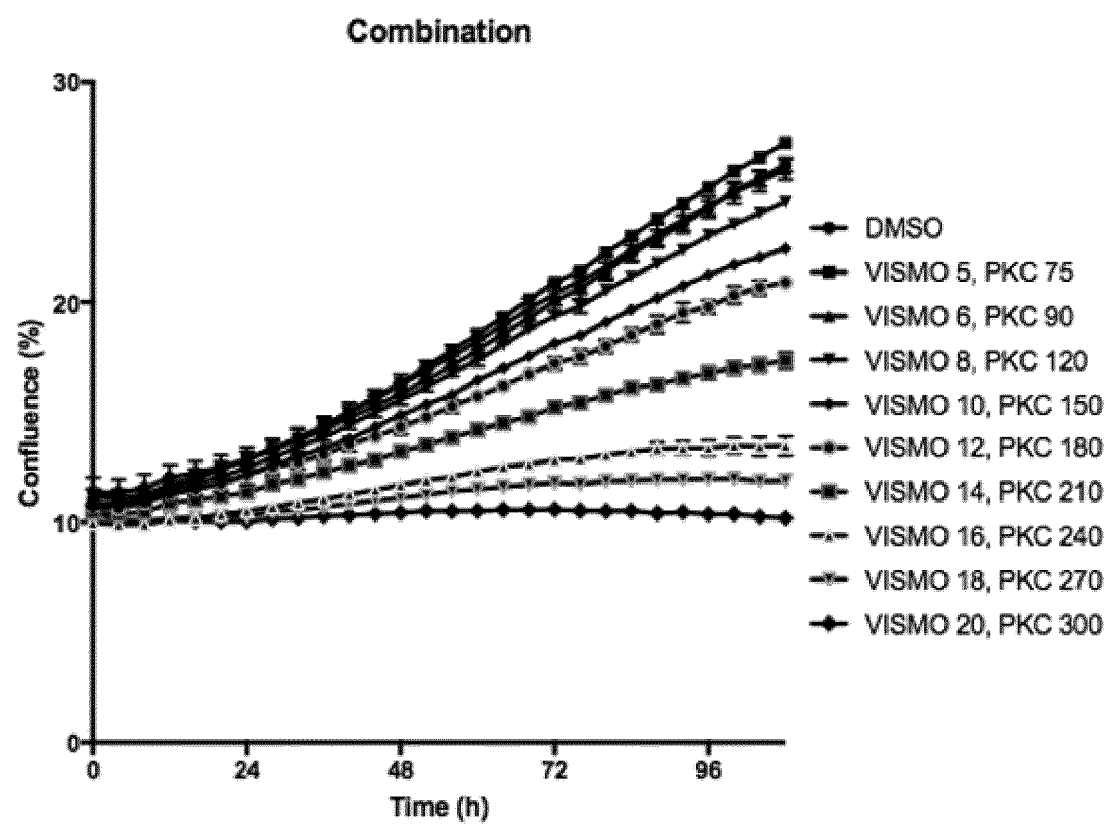

FIG. 7. Combination effects of PKC412 and Vismodegib on cell growth of ROSA KIT 417 mast cells using Incucyte cell imaging system Different doses of Vismodegib and PKC412 (Midostaurin) were combined to treat ROSA 417 cell line to determine their effects on cell growth. Analysis show that vismodegib 20 uM combined to PKC412 300 nM inhibits totally ROSA K417 proliferation.

Figure 8:
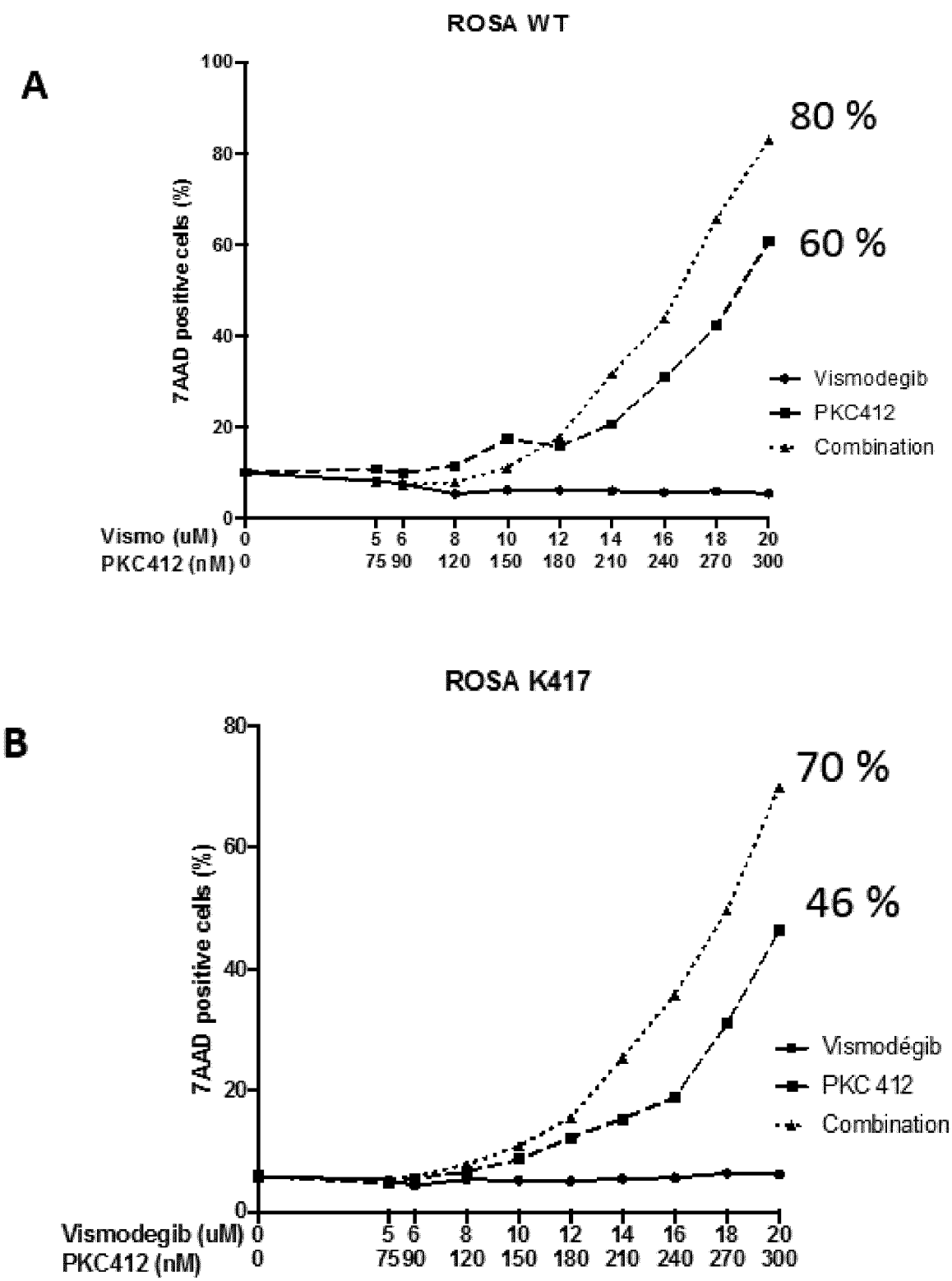

FIG. 8. Combination of PKC412 with Vismodegib increases significantly the cell death of ROSA WT and ROSA 417 as compared to PKC412 alone or vismodegib alone. A) Combination of PKC412 300 nM with Vismodegib 20 uM induces 80% cell mortality in ROSA WT. B) Combination of PKC412 300 nM with Vismodegib 20 uM induces 70% cell mortality in ROSA 417.

EXAMPLE

Methods
Cell Cultures

Different mast cell types (primary mast cells derived from cord blood CD34+ cells, the human MCL-derived cell lines HMC-1, 3 established human mast cell lines ROSA-WT and ROSA-D816V, ROSA KIT Delta 417-419 insY (Saleh R et al, A new human mast cell line expressing a functional IgE receptor converts to tumorigenic growth by KIT D816V transfection Blood 2014) and leukemic mast cells sorted from the peripheral blood of a mastocytosis leukemia patient were used to show the implication of Hedgehog signaling pathway in mast cell proliferation and to demonstrate the potential of Hedgehog inhibitors on proliferation arrest and apoptosis. The human MCL-derived cell line HMC-1 was kindly provided by Dr. Michel Arock, Paris, France. Two sub-clones were used, namely HMC-1.1 expressing KIT V560G, and HMC-1.2 expressing KIT V560G and KIT D816V.

Human primary mast cells, patient's leukemic mast cells and ROSA KIT-WT cell line were cultured in Iscove's modified Dulbecco's Medium (IMDM)-Glutamax® (Invitrogen) supplemented with the penicillin/streptomycin 100 U/ml (P/S) (Invitrogen), 1% of sodium pyruvate (Invitrogen), 1% of vitamins (Invitrogen), 1% of glutamine (Invitrogen), 2% of non-essential amino acids (Invitrogen), 1% of a commercial solution of insulin-transferrin-sodium selenite (Invitrogen), 0.3% of albumin bovine (BSA) in presence of human SCF at 100 ng/ml (Milteny biotech). "ROSA KIT D816V", "ROSA KIT Delta 417-419 insY" mast cells and HMC-1 lines which have mutated KIT receptor (CD117) grow in the same media described above but in absence of hSCF.

Western Blot and RT-qPCR:

After an overnight starvation of 5 million cells from each kind of cells described above, cells were treated with different doses of chemical agonists (such as purmorfamine) or antagonists (such as Gant61) of HH pathway and for several time-laps. Cells were then collected to extract RNA or proteins to perform gene expression analysis by RT-qPCR or western blot analysis. Hedgehog genes Gli1-2-3, Smo, Patch receptors, SHH-IHH-DHH ligands and the tumor supressor Bcl2 gene were investigated. Hedgehog proteins (Gli1 and Gli3), proteins involved in apoptosis (Bcl2, caspase3, Bcl-xl) and in PI3K/AKT/mTOR pathway were investigated.

Cell Proliferation and Apoptosis Assays

Kinetic cell proliferation assays were performed using the IncuCyte® Live Cell analysis system with 10 000 cells/well in triplicate and during one week in presence or absence of chemicals compounds, Gant61, Vismodegib and, individually or in combination, to determine their effect on mast cell proliferation. Compounds were added the first day at different doses and the media was not changed over the 7 days. At the end of the week, mast cells death was investigated by flow cytometry using 7-AAD viability staining solution.

Results

Expression of HH Target Genes in Mast Cells

In order to assess HH activity in mast cells (MC), we explored the expression of GLI1-2-3 genes in the different MC types: primary MC, leukemic MC and human MC lines (see Material & Methods). Preliminary results, obtained by Western blotting (FIG. 1*a*) and RT-qPCR (FIG. 1*b*), demonstrated the expression of GLI1 and/or GLI2 and/or GLI3 in the different cell types, with differential expression patterns, demonstrating for the first time the activation of the Hedgehog signaling pathway in normal and abnormal human mast cells.

Activation of Canonical Hedgehog Signaling Pathway in Mast Cells

In order to explore the HH canonical pathway in MC, we analyzed the expression of GLI1 protein following stimulation by purmorphamine, a SMO agonist, in human MC lines. GLI1 expression was clearly increased following stimulation by purmorphamine, especially following 24 hours of stimulation in ROSA KIT D816V (FIG. 2). These primary results led us to explore the consequence of the inhibition of the HH pathway, especially the canonical pathway, on MC proliferation.

Inhibition of hedgehog signaling pathways inhibits mast cells proliferation and induces apoptosis.

Inhibition of HH signaling pathway, via increasing doses of vismodegib (10, 20, 50 µM), prevented the proliferation of ROSA cell lines, in a dose-dependent manner (FIG. 3). This inhibition was more spectacular in KIT mutated ROSA cell lines (ROSA KIT D816V and K417) than in ROSA KIT WT cell lines (FIGS. 3*b* and 3*c*).

The MC proliferation was also inhibited following treatment with GANT61. This inhibition was more dramatic than the inhibition by vismodegib and the effect was also greater in KIT mutated ROSA cell lines (FIG. 4). In addition to inhibiting cell proliferation, GANT61 led to mast cells death. This cell death was dose dependent ranging from 5% (GANT61 5 µM) to more than 90% (GANT61 50 µM, data not shown). Interestingly, GANT61 induced leukemic MC death too (data not shown).

Whatever the cell type, this induction of cell death was much less important with vismodegib than with GANT61 (data not shown).

Involvement of Hedgehog Pathway in Mastocytosis

The FIG. 5 shows the expression analysis of GLI transcription factors in different mast cell lineages carrying or not KIT-D816V mutation.

The FIG. 6 shows that GANT61 inhibits mast cells proliferation and induces mast cells apoptosis.

The FIG. 7 shows the combination effects of PKC412 and Vismodegib on cell growth of ROSA KIT 417 mast cells using Incucyte cell imaging system.

The FIG. 8 shows that combination of PKC412 with Vismodegib increases significantly the cell death of ROSA WT and ROSA 417 as compared to PKC412 alone or vismodegib alone.

REFERENCES

Throughout this application, various references describe the state of the art to which this invention pertains. The disclosures of these references are hereby incorporated by reference into the present disclosure.

The invention claimed is:

1. A method of treating mastocytosis in a patient in need thereof comprising administering to the patient a therapeutically effective amount of a Hedgehog inhibitor, wherein the therapeutically effective amount is an amount sufficient to inhibit mast cell proliferation.

2. The method of claim 1 wherein the mastocytosis is selected from the group consisting of cutaneous mastocytosis; systemic mastocytosis; and systemic indolent mastocytosis.

3. The method of claim 1 wherein the pathogenesis of mastocytosis is attributed to constitutive activation of the receptor tyrosine kinase KIT.

4. The method of claim 1 wherein the Hedgehog inhibitor is vismodegib or GANT61.

5. The method of claim 1 wherein the Hedgehog inhibitor is administered to the patient in combination with a tyrosine kinase inhibitor selected from the group consisting of PKC412 (midostaurin), afatinib, alitretinoin, axitinib, bafetinib, bexarotene, BI-2536, bosutinib, brivanib, canertinib, cediranib, CP724714, crizotinib, dasatinib, danusertib, dovitinib, E7080, erlotinib, everolimus, fostamatinib, gefitinib, imatinib, lapatinib, lestaurtinib, linsitinib, masitinib, motesanib, neratinib, nilotinib, NVP TAE-684, OSI-027, OSI-420, OSI-930, pazopanib, pelitinib, PF573228, regorafenib, romidepsin, ruxolitinib, saracatinib, sorafenib, sunitinib, TAE226, TAE684, tandutinib, telatinib, tautinib, temsirolimus, toceranib, tofacitinib, tozasertib, tretinoin, vandetanib, vatalanib, vemurafenib, vorinostat and WZ 4002.

6. The method of claim 3, wherein the constitutive activation of the receptor tyrosine kinase KIT is due to a KIT mutation.

7. The method of claim 1, wherein the patient does not have cancer.

* * * * *